United States Patent [19]

Batters

[11] Patent Number: 4,664,118
[45] Date of Patent: * May 12, 1987

[54] ELECTRICAL THERAPEUTIC ASSEMBLY AND METHOD FOR REDUCING PAIN AND EDEMA IN A HUMAN BODY

[76] Inventor: Robert C. Batters, 3125 Boulder Way, Eastpoint, Ga. 30344

[ * ] Notice: The portion of the term of this patent subsequent to Nov. 26, 2002 has been disclaimed.

[21] Appl. No.: 663,728

[22] Filed: Oct. 22, 1984

Related U.S. Application Data

[63] Continuation of Ser. No. 413,103, Aug. 30, 1982, Pat. No. 4,554,923.

[51] Int. Cl.4 .............................................. A61N 3/06
[52] U.S. Cl. ..................................... 128/421; 128/79; 128/802
[58] Field of Search ................. 128/798, 800, 26, 796, 128/421, 422, 802

[56] References Cited

U.S. PATENT DOCUMENTS

| | | | |
|---|---|---|---|
| 1,975,518 | 10/1934 | Rose | 128/798 |
| 3,543,760 | 12/1970 | Bolduc | 128/798 |
| 3,817,253 | 6/1974 | Gonser | 128/798 |
| 3,845,771 | 11/1974 | Vise | 128/800 X |
| 4,213,463 | 7/1980 | Ozenkarski | 128/798 X |
| 4,510,939 | 4/1985 | Brenman et al. | 128/800 X |

Primary Examiner—Edward M. Coven
Attorney, Agent, or Firm—Neil F. Markva

[57] ABSTRACT

An electrical therapeutic assembly and method for reducing pain and edema in a human body uses an electrically conducting material contiguously disposed with respect to the skin on an area enveloped by said conducting material. The skin is free of any externally applied mediums so that there is a substantially dry contact between the skin and the electrically conducting medium. A substantially uniform electric current is passed throughout the entire conducting medium to apply the current to the enveloped area. The electric current is applied at a shock pulse rate sufficient to reduce pain in the enveloped area without causing heat build-up within the tissue of the human body. A particular feature of the assembly makes use of a woven, mesh metal material that is in direct contact with the area of the human body and effective to apply electrical shock pulses of the entire and enveloped area. The metal mesh material is in the form of a glove for enveloping a hand, a sock to envelope the foot and ankle, a sleeve for enveloping joints such as elbows and knees or in the form of a sheet or a blanket which may be wrapped around any portion of the body.

20 Claims, 7 Drawing Figures

U.S. Patent  May 12, 1987  Sheet 1 of 2  4,664,118
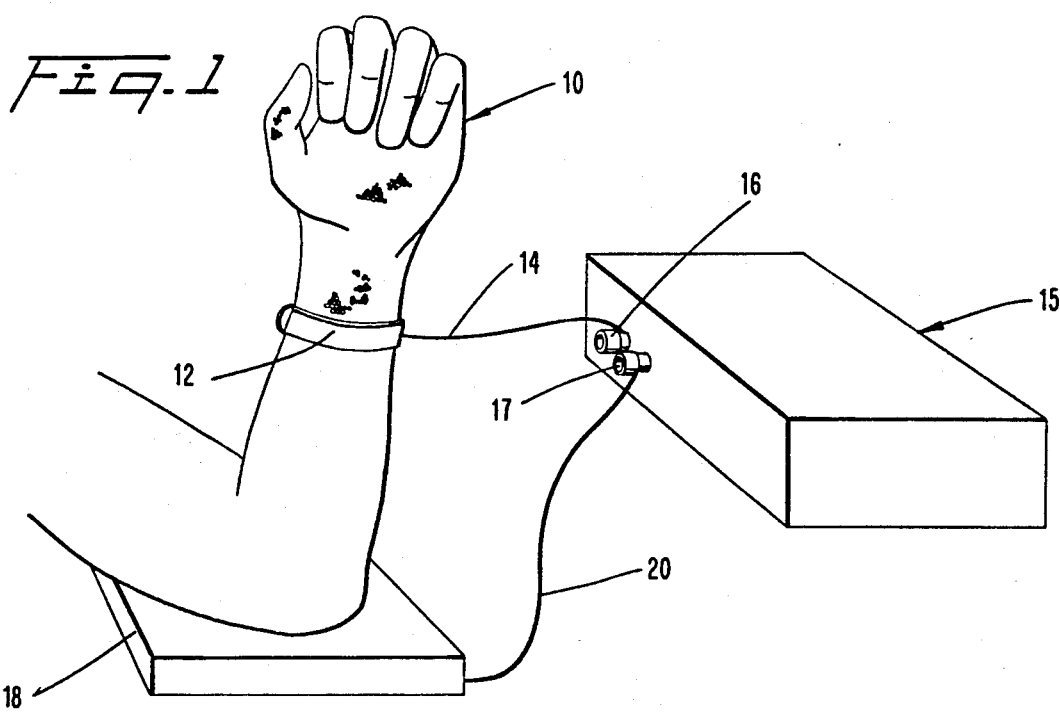
Fig. 1
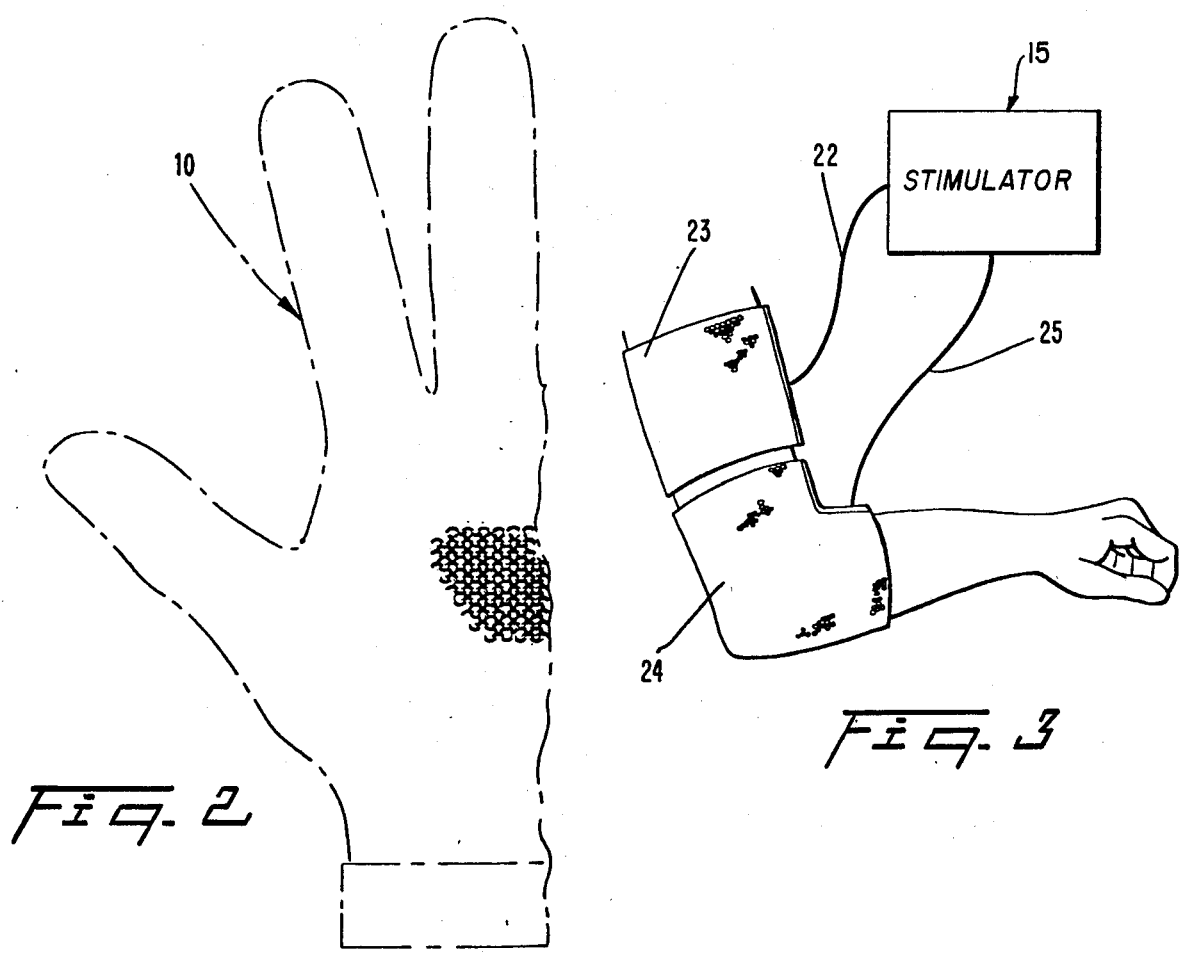
Fig. 2
Fig. 3

ELECTRICAL THERAPEUTIC ASSEMBLY AND METHOD FOR REDUCING PAIN AND EDEMA IN A HUMAN BODY

This a continuation, of application Ser. No. 413,103, filed Aug. 30, 1982, now U.S. Pat. No. 4,554,923.

FIELD OF THE INVENTION

This invention is related to the therapeutic treatment of the hand of the human body subjected to pain due to inflammation, trauma, or operative procedures. More particularly, the invention is directed to the treatment of painful areas of the human hand through the use of electrical shock pulses.

BACKGROUND OF THE INVENTION

The treatment of painful areas on the human body with electrical shock pulses is well known. The U.S. Pat. No. 1,583,087 discloses a known electrical therapeutic apparatus wherein a pad member is moistened and placed on any portion of the body and connected to an electrical circuit so that the patient will receive the desired electrical treatment. In this instance, the pad terminal comprises a metal plate and a particular type of mounting to accomodate an absorbent material used as a pad in combination with the metal plate.

The U.S. Pat. No. 3,055,372 discloses a device for the electrical treatment of body tissues which includes electrically conductive rubber electrodes for producing pulsations to muscles in the human body. Pairs of pads are required to apply such pulsations which are received through the use of a variable speed motor. This prior art device is used just to improve the tone and general health of the body parts. There is no disclosure of this device being able to reduce pain and edema in the human body.

The U.S. Pat. No. 4,014,345 discloses an electrode having a metal plate used in combination with a sponge which is used in a wet condition to apply low current electrical pulse signals to stimulate body nerves with the effect that pain and other circulatory difficulties might be relieved. This electrode has a retaining ring and a very specific interrelationship between the sponge, metal plate and retaining ring to achieve the results desired by the patentee in that instance.

The U.S. Pat. No. 3,817,252 discloses another type of electrode for transcutaneous stimulation with electrical impulses. In this prior art structure, the electrode incorporates the use of a wet sponge and is particularly made to be a disposable electrode. An interface pad is made of a foam material and is expressly used to prevent the direct contact between the skin and the electrically conducting diffusor screen. Again, this type of an electrode makes use of an externally applied liquid medium to establish an electrical connection across the surface of the area being treated.

None of the prior art electrodes used to apply electrical shock pulses to the human body are satisfactory to diminish pain in joints such as the knuckles of the hand, elbow, knees, ankles, toes and the like. Particularly, people who have had operations as a result of fractures in the hand generally experience much pain. This occurs because one-fourth of all the sensory nerves in the body are located in the hands. Consequently, they are extremely sensitive. An injury to a joint in the hand can produce such pain that the patient refuses to move the body part and can lead to a condition called "causalgic" hand.

A major disadvantage associated with prior art efforts as they are applied to edematous joints of the hands is: avoidance of a dependent position or placing the body part lower than the heart, which encourages still more edema. Thus, it is necessary to elevate the body part to treat edema which occurs as a result of pain.

When tissue is traumatized, fluid rushes to that area to swell the joint to limit motion so that the person will not cause further damage. The body provides its own splinting mechanism. For example, if a thumb is hit with a hammer, it immediately swells up so that the person cannot move their thumb and injure themselves more if a bone happened to be broken. Once edema has formed in the joint, its removal is a significant problem. The current treatment is to apply ice, compression and elevation (I.C.E.). This is the accepted first aid as administered with injuries involving soft tissue trauma. The chief concern is prevention of swelling so that an appropriate examination can be performed.

Another area of need in the prior art is an improved method of treating phantom pain which occurs in conjunction with a prosthesis being worn on the stump. Currently, if someone is suffering from phantom pain, use of the prosthesis is limited. That is, treatment of the phantom pain is limited to the time when the prosthesis is not being worn. Thus, the person is not able to function during such treatment. The present treatment requires the use of a gel or lubricant which acts as an electrically conducting medium for a postage stamp size electrode which is taped in place on the stump. A transcutaneous electrical nerve stimulator (TENS unit) is electrically connected to the electrode and electrical stimulation is thus applied directly to the stump. Such TENS units are very well known and readily available from numerous sources. It is about the size of a cigarette package and may be worn on the belt.

The prior art devices as discussed all require lubricant or some kind of an electrical medium to be applied to the skin for the purpose of providing an electrical shock or stimulation to the surface of the skin. One of the basic problems associated with such use of a wet lubricant is that the skin tissue becomes mottled or macerated when there is a prolonged use of the electrode in conjunction with the gel or lubricant. This problem is especially present when the prior art electrodes are used with a prosthesis which simply adds to the application of pressure on the skin area being treated.

The prior art electrodes used to apply electrical shock pulses to areas on the human body do not permit total conformity to the body part, and elevation of the injured area. Electrodes now being used to control pain and edema cover a smaller part of the involved area and offer a nonuniform impulse and associated discomfort when using higher voltages. The electrodes being used for applying electrical stimulation to body portions are either a two by two inch square plate with a sponge on it or a four by four inch type pad having a sponge conforming to a metal electrode. In both instances, the electrodes are either strapped or taped onto the body part to which the electrical stimulation is being applied. When a sponge is used it is in a wet condition in order to cause the current to be conducted to the surface of the skin. The prior art electrodes require the use of a gel or cream or some other type of lubricant so that there is no direct contact between the metal electrode itself and the surface of the skin. If the metal electrode were placed in direct contact with the skin, there would be an uncomfortable feeling of a prickly sensation or an uncomfortable electrical shock type of feeling. Known prior art electrodes are not capable of conforming to a joint such as a hand, foot, elbow, knee or the like.

In most recent developments, it has been found that the best possible way to treat a limb or joint post operatively is to have constant motion at the joint. That is, such motion has been found to enhance circulation at the joint and thereby significantly speed up the healing process. Because the prior art electrodes have to be strapped on or taped in place in such a manner that they do not conform to the joint itself, such a desirable joint motion is significantly limited. Thus, the recommended treatment of traumatized joints through the effecting of movement is severely limited.

Purpose of the Invention

The primary object of the invention is to provide a method and an apparatus for effecting treatment of an injured area on a human body without having to effect any external application of a liquid medium such as a salve, gel or water to establish a substantially uniform electric current over an extended area of the body.

Another object of the invention is to provide a method and an apparatus for treating highly sensitive areas such as the hand so that all of the joints of the hand may be treated simultaneously while the part is held in an elevated position for the reduction of pain and edema in the joints.

A further object of the invention is to provide a method and apparatus for treating joints in the human body which have been subjected to trauma or have been subjected to surgery for the purpose of relieving pain and edema therein without danger of heat buildup in the tissues of the body while maintaining a substantially uniform application of electrical shock pulses over the entire area enveloped by the apparatus of the invention.

Furthermore, the object of this invention is to provide an electrode which does not limit or impair range of motion from being performed actively or passively thereby allowing a further means of inhibiting joint pain, edema, and stiffness.

A further object of the invention is to overcome the disadvantages associated with the known types of electrodes and electrical nerve stimulators which are presently available for treatment with electrical shock pulses.

SUMMARY OF THE INVENTION

As disclosed and described herein, the method of the invention comprises the steps of enveloping the area of the body to be treated with an electrically conducting material contiguously disposed with respect to the skin of the human body. The skin is free from any externally applied liquid medium so that there is a substantially dry contact between the skin and the electrically conducting material. The electrically conducting material is then electrically connected to a source of electric current and a substantially uniform electric current is passed throughout the entire conducting material to apply the current directly to the enveloped area. The electric current is applied at a shock pulse rate sufficient to reduce pain in the enveloped area without causing heat build-up within the tissue of the human body.

A particular feature of the invention with the use of a galvanic current is in applying the positively charged current to the electrode. This technique will drive the fluid within the area being treated away from the area of the pain. The electric current may be generated using a relatively high voltage of from about 200 to 525 volts while providing a microamperage current being applied at a pulse rate of from about 2 to 128 pulses per second. The pulse width is in the range of from about 150 to 350 microseconds.

The electrical therapeutic assembly of the invention comprises a woven, metal mesh material which is sufficiently flexible to envelope an area of the body in which there is pain. Electrically connecting means are used to connect the woven, metal mesh material to a source of electric current. The mesh material is effective to conduct a substantially uniform current over the entire area enveloped by the material to apply electric shock pulses directly to the enveloped area. The mesh material is further effective to produce the electrical shock pulses without causing heat build-up within the tissue of the human body and without the necessity of having an externally applied liquid medium on the skin of the enveloped area. Electrical connecting means include contact means fixed to the mesh material and clip contacts for electrically contacting the mesh material at any available location thereon. The latter type of connecting means may be effected after the mesh material has been placed around the area to be treated. This therefore makes the assembly an extremely versatile type of an electrode particularly in the treatment of areas such as hands, elbows, knees, feet and ankles.

A further feature of the invention is to have a flexible, elastomeric material disposed around the mesh material to enhance the physical contact between the mesh material and the skin over the area of the human body to be treated. In one embodiment, the elastomeric material is integrally formed around the side of the mesh material that is not in direct contact with the skin.

A further feature of the invention is directed to the particular shape of the mesh material to fit the peculiarities of the various joints. Thus, the mesh material may be in the form of a glove when treating a hand, the form of a sock for treating the foot and ankle, the form of a sheet or blanket when treating large areas such as the back and in the shape of a sleeve which might be slipped over an elbow or knee. A fine wire mesh in the form of a wire cloth is useful in treating phantom pain which may occur with a prosthesis.

BRIEF DESCRIPTION OF THE DRAWINGS

Other objects of this invention will appear in the following description and appended claims, reference being made to the accompanying drawings forming a part of the specification wherein like reference characters designate corresponding parts in the several views.

FIG. 1 is a perspective view showing the treatment of a hand with an electrode made in accordance with this invention;

FIG. 2 is a fragmentary elevational view showing an electrode for a hand made in accordance with this invention;

FIG. 3 is an elevational view of an electrode assembly useful for treating an elbow in accordance with this invention;

DETAILED DESCRIPTION

Figure 4:
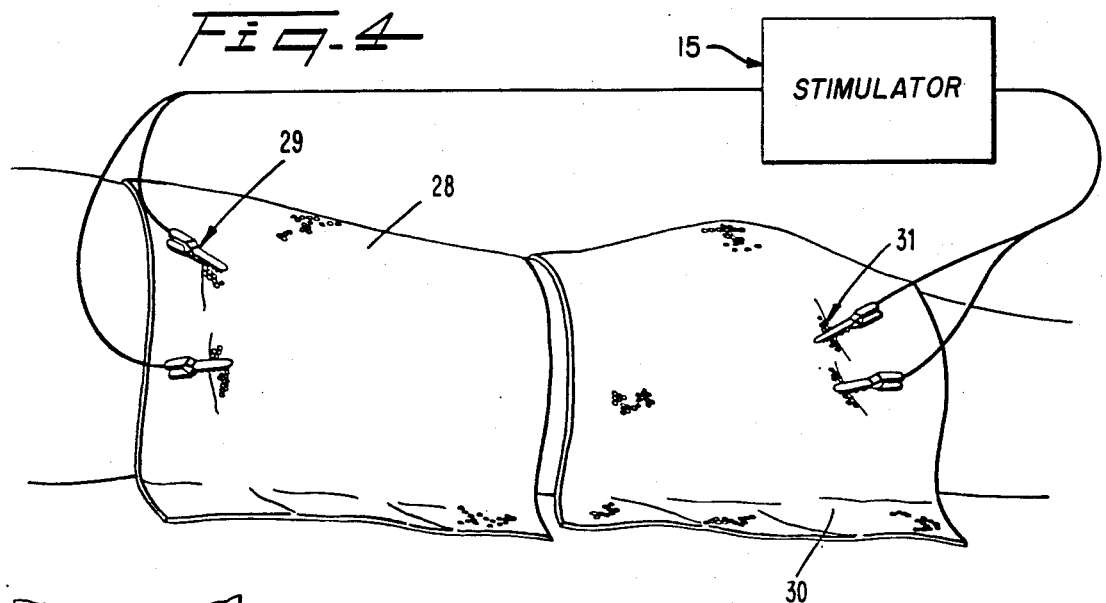
FIG. 4 is an elevational view showing the treatment of a back area of a patient with a blanket electrode made in accordance with this invention.

The electrical therapeutic assembly as shown in FIG. 1 includes an electrically conducting material in the form of a glove 10 for enveloping the hand of a human body. Glove 10 is made of a woven, metal mesh material which is sufficiently flexible to envelope the entire hand and completely surround all the joints. The fine metal mesh glove 10 is composed of a series of loops as clearly shown in FIG. 2. The metal may be stainless steel, brass or aluminum. Glove 10 may be a safety glove marketed under the trademark Niroflex or manufactured by Whiting & Davis Co. of Plainsville, Mass. A strap 12 is disposed at the wrist and includes a Velcro fastening mechanism for holding glove 10 in place on the patient's hand. Glove 10 acts as a first electrode operating in conjunction with the electrical pulse producing device 15.

During treatment, the patient places his elbow on a second electrode 18. The second electrode may be any other type of electrode which is already available in the prior art such as a metal pad as discussed above. It might also be another piece of woven, mesh material. A lead 20 connects electrode 18 to the device 15. Coupling members 16 and 17 may be composed of any type of standard electrical connecting device such as a jack for connecting the leads 14 and 20, respectively, to the electrical pulse producing device 15.

Stimulating device 15 may be composed of a portable pulsed galvanic stimulator which produces a pulse rate of current of from about 2 to about 128 pulses per second. The pulse width may be from about 150 to about 350 microseconds. The rate of electric current from device 15 is measured in microamperage at a voltage in the range of from about 200 to about 525 volts. Such a stimulator is readily available and manufactured by Staodynamics, Inc. Another high voltage medical electronic pulser made by Dynawave Corporation of Geneva, Illinois produces high voltage unidirectional, short duration, twin-peaked pulses. The twin pulse repetition rate is selectable of from 1 to 105 cycles per second. The pulse amplitude is voltage controlled and adjustable from 0 to 500 volts maximum with 500 microamps being a maximum current flow.

In a system of the type shown in FIG. 1, device 15 produces short duration pulses of electric current which are applied directly through an active electrode, which in the case of this invention, is the metal glove 10. The dispersive or inactive electrode 18 is connected to any convenient portion of the body that has enough mass and area to carry the current without excessive stimulation of this particular portion.

According to the prior art, bare metal against the skin does not ordinarily make a low resistance connection which is required in this type of therapy. Consequently, in the prior art methods, to assure low resistance, it is necessary to moisten the skin at the point at which the active electrode is to be placed. With the prior art methodology, the active electrode must be moved from point to point during treatment of the patient. Consequently, the applicator associated with the electrode must carry a considerable amount of moisture to make sure that there is a wet contact between the electrode and the skin. One of the problems of this prior art method is that the sponge used to hold the moisture may contract when it is dry and split if the threads are allowed to dry on the electrode.

However, with the use of a woven, metal mesh material such as found in the glove 10, it is no longer necessary to use a moisture containing material such as a sponge for having a wet contact. That is, the skin on the hand is free from any externally applied medium so that there is a substantially dry contact between the skin and the electrically conducting material. This clearly overcomes several problems associated with the prior art methods as discussed above. Once the glove 10 is electrically connected to the stimulating device 15, a substantially uniform electric current is passed throughout the entire conducting material along the various strands of the mesh to apply the current to the enveloped area of the body. In this instance, glove 10 envelops the entire hand and all of its joints. The current is applied at a shock pulse rate sufficient to reduce pain in the enveloped area without causing heat build-up within the tissue of the human body. In a specific embodiment, the pulse rate of current has been used at about 8 pulses per second. The voltage of the device 15 is set at about 500 volts with an extremely low rate of current flow measured in microamps.

When glove 10 is a positive electrode, it is effective to reduce edema within the enveloped area of the body. That is, the fluid in the body has a positive charge. Thus, when the electrode has a positive charge it will repel the fluid in the body and cause it to move away from the swollen joints. On the other hand, if glove 10 constitutes a negative electrode it is effective to soften tissue within the enveloped area of the body.

The woven, mesh glove 10 enables the patient to hold his hand elevated as shown in FIG. 1. At the same time, with the use of the novel electrode 10, the patient is able to flex and move the joints of his hand during treatment in the elevated position. This result has never before been achievable using the electrodes of the prior art. The electrode glove 10 is totally conformable to the joints of the hand and the wire mesh is flexible enough that the active and passive range of motion can be carried out without any hinderence. Thus, circulation is enhanced and the healing process is greatly expedited.

Unlike prior art electrodes which are operating only in a local area on the body, the electrode glove 10 which conforms exactly to the joints of the hand, gives a uniform current to the joints instead of a localized current thereby preventing any build-up of current in a local area and a nonuniform application to the joint. The totally enveloped joint receives a uniform current and has a much more comfortable sensation. With the electrode glove 10, higher currents may be used without adversely affecting the body tissue that is enveloped. This is unlike the typical prior art electrodes where there is a build-up of current at one point thus significantly limiting the amount of current that may be used.

It is possible to treat the patient with either alternating or direct current. However, using alternating current it is not possible to treat the swelling or edema in the fashion described with the galvanic or direct current application. When using a pulse rate setting of 2 pulses per second, the pulse width is 350 microseconds.

At 8 pulses per second, the pulse width is 250 microseconds and at 128 pulses per second, the pulse width is 150 microseconds.

The new and unexpected results flowing from the use of the woven, mesh glove 10 includes the overcoming of all the disadvantages associated with the prior art electrodes as discussed above. With such a woven, mesh material it has been found that, contrary to the prior art electrodes, no moisture or liquid is necessary to achieve the desired electrical current pulses which envelope the entire joint. In contrast, the prior art electrodes must necessarily be inclusive of a moisture producing pad or sponge material. The results of reduction of pain and swelling have been significant. Furthermore, the patient may be able to perform treatments on his own without supervision from a doctor or therapist. This is an extremely significant development in the treatment of pain and swelling for patients because such treatment is now available on a broad basis in the patient's home rather than by skilled therapists at a location other than their home.

The discovery of using a woven, wire mesh material as an electrical conducting material is extremely significant when treating other joints such as elbows and ankles. FIG. 3 shows a positive, active electrode 24 which envelopes the elbow joint and an inactive or dispersive electrode 22 slightly spaced from the positive electrode. Leads 22 and 25 electrically connect the respective electrodes 23 and 24 to a stimulating device 15 such as discussed in conjunction with FIG. 1.

Figure 5:
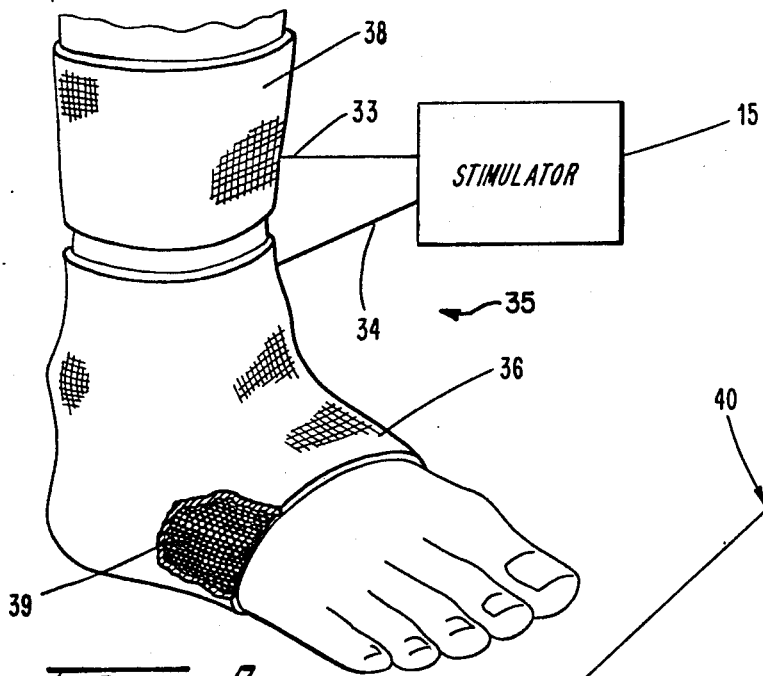
FIG. 5 is a perspective view of an electrode assembly used in treating of an ankle joint in accordance with this invention.

In FIG. 5, a single electrode assembly 35 is shown having two woven, mesh electrodes 38 and 39 laterally spaced with respect to each other and in direct contact with the area surrounding the ankle. Electrodes 38 and 39 are embedded in an elastomeric type material 36 which is formed as a tubular sleeve and designed specifically for sliding over the foot onto the ankle of the patient. Electrical leads 33 and 34 connect electrodes 38 and 39, respectively, to the negative and positive contacts of a stimulator device 15 as shown in FIG. 1. The woven, mesh material forming electrodes 38 and 39 are integrally molded into the elastomeric material 36 so that there is a firm, dry electrical connection existing between the woven, mesh material and the skin of the patient.

A further new and unexpected result flowing from the use of a woven, mesh material as a dry contact electrode enables the instantaneous treatment of trauma patients such as in accidents attended to by emergency units and injuries suffered during athletic events. With the discovery of the electrode of this invention, it is now possible to provide instantaneous treatment directly at the site of the accident or injury. With such trauma, swelling is a problem that needs to be addressed immediately. With the electrode of the present invention, it is possible to use a high voltage in combination with a microamperage, galvanic current so that both pain and swelling can be treated immediately. The available transcutaneous electrical nerve stimulators (TENS units) which are already known for treating pain may be used to produce the stimulation through the woven, mesh electrode of the present invention. This will produce a much more uniform and effective stimulation for reducing pain. Wire mesh may be formed as a sock or a sleeve and applied with an Ace bandage or an elastic stocking to apply a galvanic current for controlling the swelling in a joint injured on an athletic field or an accident. This is an alternative to the type of sleeve mechanism shown in FIG. 5. An elastic stocking would promote more compression between the wire mesh electrode and the joint being treated for enhancing the type of stimulation achieved using stimulators that are available in the prior art.

The electrical connection may be fixed to the mesh material or may involve the use of clip contacts for electrically contacting the mesh material at any available location. In FIG. 4, large blanket type electrodes 28 and 30 are shown draped over the back of a patient. A plurality of alligator clips 29 and 31 electrically connect a stimulating device 15 to the separated woven, mesh blankets 28 and 30. The plurality of alligator clips enables the application of current to a plurality of places on the blankets 28 and 30 thus assuring a substantially uniform flow of current throughout the entire mesh material. One of the electrodes 28 and 30 is active and the other one passive depending upon the specific area that is desired to treat with electrical pulse stimulation.

A copper wire twisted into the woven mesh may be used to electrically connect the woven, mesh glove 10 to the stimulator 15. In the embodiment shown in FIG. 3, the electrodes 23 and 24 may be formed as a sleeve or as a sheet wrapped around the arm and held in place with a strap device such as a Velcro band or an Ace bandage. If the woven wire mesh is in a sheet, then it is possible that the electrical connection can be made simply using alligator clips at the end of the leads 22 and 25 to attach at any convenient location on the respective electrode.

With the woven, mesh glove 10, the patient need not immerse his hand in water such as has been the practice with prior art electrodes when treating the hand.

Figure 6:
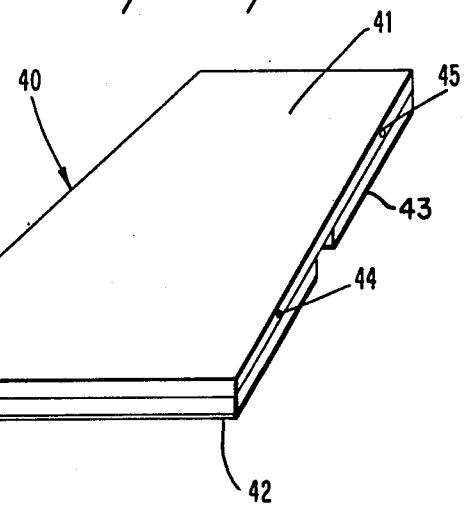
FIG. 6 is a perspective view of an electrode made in accordance with this invention.

The construction of an electrode contemplated by this invention is shown in FIG. 6. An electrode assembly 40 includes a pair of woven, wire mesh electrode pads 42 and 43 which are laterally spaced with respect to each other. The electrodes 42 and 43 are integrally formed in an elastomeric layer 41 which also includes electrical connecting jacks 44 and 45 to electrically connect the electrodes 42 and 43, respectively, to a stimulating device. Electrode 40 may be wrapped around a joint such as an elbow joint shown in FIG. 3 in place of using two separate electrodes. Electrode assembly 40 may be held in place using a Velcro fastening mechanism or other type of strap material. The electrodes 42 and 43 are held in contiguous, dry contact with the skin of the area being treated.

Figure 7:
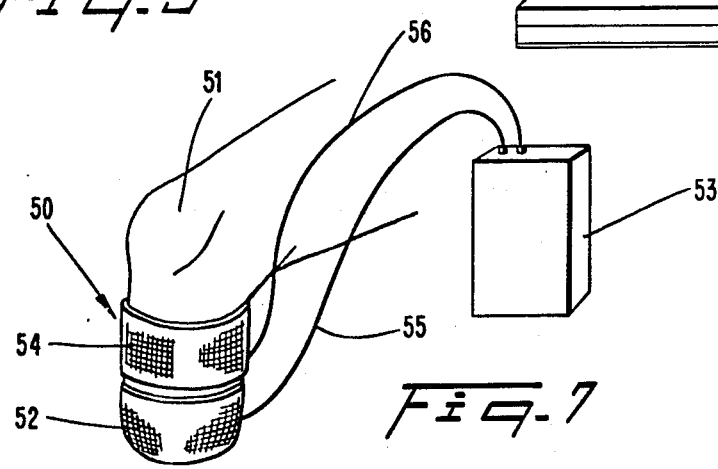
FIG. 7 is an elevational view showing the use of an electrode made in accordance with this invention in conjunction with a prosthesis.

In FIG. 7, another embodiment of the invention shows the use of a very fine woven, wire metal mesh material for treating phantom pain resulting with use of a prosthesis. In this embodiment, a sock assembly 50 has a fine wire mesh electrode 52 shaped to fit over the end of the stump 51. Laterally spaced from electrode 52 is a second wire mesh electrode 54 which constitutes the inactive or dispersive electrode. In this specific embodiment, the wire mesh size has about 500 strands per inch and each wire strand has a diameter of about 0.0026 inch.

Different size wire meshes may be used depending upon the particular application. However, with the 500 mesh wire cloth, it is deemed possible to have the electrode 52 in place while the prosthesis is in place. This constitutes a significant improvement over anything in the prior art which requires the complete removal of the prosthesis during treatment using small electrodes used in combination with the liquid material as discussed above.

The electrodes 52 and 54 are connected to a TENS unit 53 via electrical leads 55 and 56, respectively. When attached to a galvanic type of a unit, it would then also be possible to control edema in the stump along with controlling any phantom pain. Assembly 50 in FIG. 7 is shown with separate electrodes mounted on the inside of a sock member. However, the sock itself could be completely formed using the wire mesh material. Such wire mesh may be a cloth having from about 150 to about 500 wire strands per inch and the diameter of the wire strands being from about 0.0014 to about 0.0026 inch.

With the electrode of this particular invention, a stimulator unit is worn directly on the person and directly connected to a stump sock made in accordance with this invention. Thus, pain and swelling may be controlled while the prosthesis is in use. Further, this invention would eliminate any wear spots on the stump and avoid any breakdown of the skin. The cloth conforms totally to the stump and does not act as a foreign object inside the prosthesis.

While the electrical therapeutic assembly and method for reducing pain and edema in a human body has been shown and described in detail, it is obvious that this invention is not to be considered as being limited to the exact form disclosed, and that changes in detail and construction may be made therein within the scope of the invention, without departing from the spirit thereof.

Having thus set forth and disclosed the nature of this invention, what is claimed is:

1. A method of reducing pain in a human body, said method comprising the steps of:
   (a) enveloping the area of the body to contiguously dispose an electrically conducting flexible, metal mesh material directly to the skin of the human body,
   (b) wrapping a flexible, elastomeric material over the metal mesh material to enhance the direct contact between the metal and the skin at the area being treated,
   (c) electrically connecting the metal mesh material to a source of electric current,
   (d) passing a substantially uniform electric current throughout the entire metal mesh material to cause electrical shock pulses to be applied to the skin within said enveloped area,
   (e) said current is applied at a shock pulse rate sufficient to reduce pain in said enveloped area without causing heat buildup within the tissue of the human body.

2. A method as defined in claim 1, wherein the pulse rate of current is from about 2 to about 128 pulses per second.

3. A method as defined in claim 2, wherein the pulse rate of current is about 8 pulses per second.

4. A method as defined in claim 1, wherein the pulse width is in the range of from about 150 to about 350 microseconds.

5. A method as defined in claim 1, wherein the rate of electric current is measured in microamperage at a voltage in the range of about 200 to about 525 volts.

6. A method as defined in claim 1, wherein the electric current is galvanic current.

7. A method as defined in claim 6, wherein the electrically conducting material constitutes a positive electrode and is effective to reduce edema within the enveloped area of the body.

8. A method as defined in claim 6, wherein the electrically conducting material constitutes a negative electrode and is effective to soften tissue within the enveloped area of the body.

9. A method as defined in claim 1 wherein the electrically conducting material includes an active electrode and a passive electrode with said active and passive electrodes being laterally spaced with respect to each other.

10. An electrical therapeutic assembly for reducing pain and edema in a human body, said assembly comprising:
    (a) a woven, metal mesh material which is sufficiently flexible to envelope an area of the body in which there is pain,
    (b) flexible, elastomeric means disposed around the mesh material to enhance the physical contact between the mesh material and the skin over the area of the human body to be treated, and
    (c) means for electrically connecting the woven, metal mesh material to a source of electric current,
    (d) said woven, metal mesh material being effective to conduct a substantially uniform current over the entire area enveloped by the material to apply electrical shock pulses directly to said enveloped area,
    (e) said mesh material being effective to produce said electrical shock pulses without causing heat buildup within the tissue of the human body.

11. An assembly as defined in claim 10, wherein the electrically connecting means includes contact means fixed to the mesh material for connecting electricity thereto.

12. An electrical therapeutic assembly for reducing pain and edema in a human body, said assembly comprising:
    (a) a woven, metal mesh material which is sufficiently flexible to contiguously, physically contact skin with one side of the mesh material and to envelope an area of the body in which there is pain,
    (b) flexible, elastomeric means disposed around the other side of the mesh material to enhance the physical contact between the mesh material and the skin over the area of the human body to be treated, and
    (c) means for electrically connecting the woven, metal mesh material to a source of electric current,
    (d) said woven, metal mesh material being effective to conduct a substantially uniform current over the entire area enveloped by the material to apply electrical shock pulses directly to the skin within said enveloped area,
    (e) said mesh material being effective to produce said electrical shock pulses without ceasing heat buildup within the tissue of the human body.

13. An assembly as defined in claim 10, wherein the elastomeric material is integrally formed around the side of the mesh material that is not to be in direct contact with the skin over the area of the human body to be treated.

14. An assembly as defined in claim 10, wherein said mesh material is in the form of a glove for enveloping the hand or parts thereof.

15. An assembly as defined in claim 10, wherein said mesh material is in the form of a sock to envelope the foot and ankle of a human body.

16. An assembly as defined in claim 10, wherein said mesh material is in the form of a sheet or blanket which may be wrapped around any portion of the body.

17. An assembly as defined in claim 10, wherein said mesh material is in the form of a sleeve for enveloping joints such as elbows and knees.

18. An assembly as defined in claim 10 wherein the electrically conducting material includes an active electrode and a passive electrode.

19. An assembly as defined in claim 18 wherein said active and passive electrodes are laterally spaced with respect to each other.

20. An assembly as defined in claim 18 wherein the passive electrode is grounded with the active electrode being effective to deliver said current to the enveloped area of the body.

* * * * *